United States Patent

Krauter et al.

Patent Number: 5,275,152
Date of Patent: Jan. 4, 1994

[54] INSERTION TUBE TERMINATOR

[75] Inventors: Allan I. Krauter, Syracuse; Terry V. Grantier, Elbridge, both of N.Y.

[73] Assignee: Welch Allyn, Inc., Skaneateles Falls, N.Y.

[21] Appl. No.: 919,843

[22] Filed: Jul. 27, 1992

[51] Int. Cl.$^5$ .................................. A61B 1/00
[52] U.S. Cl. ...................... 128/4; 174/74 R; 138/109; 604/282
[58] Field of Search .................. 128/4, 6, 772, 656, 128/657, 658, 786, 784, 642, 419; 174/74; 604/282, 283, 280; 138/127, 96; 29/854, 747, 857; 493/949

[56] References Cited

U.S. PATENT DOCUMENTS

| | | | |
|---|---|---|---|
| 2,691,058 | 10/1954 | Millar | 174/74 R |
| 4,669,172 | 6/1987 | Petruzzi | 138/131 X |
| 4,686,964 | 8/1987 | Yunoki et al. | 128/6 X |
| 4,697,870 | 10/1987 | Richards . | |
| 4,753,222 | 6/1988 | Morishita | 128/4 |
| 4,788,967 | 12/1988 | Ueda . | |
| 4,805,595 | 2/1989 | Kanbara | 128/4 |
| 4,895,138 | 1/1990 | Yabe | 128/6 |
| 4,899,787 | 2/1990 | Ouchi et al. | 138/131 |
| 4,946,442 | 8/1990 | Sanagi . | |
| 4,989,581 | 2/1991 | Tamburrino et al. . | |
| 5,170,775 | 12/1992 | Tagami | 128/4 |

FOREIGN PATENT DOCUMENTS

| | | | |
|---|---|---|---|
| 2283346 | 11/1990 | Japan | 128/4 |

*Primary Examiner*—Richard J. Apley
*Assistant Examiner*—Karen A. Jalbert
*Attorney, Agent, or Firm*—Wall and Roehrig

[57] ABSTRACT

The insertion tube body of a borescope or endoscope is constructed to avoid leakage current. An inner coil is covered with a tubular urethane jacket over which a tubular braid is disposed. Terminators having sleeve portions are attached by inserting the sleeve portions between the coil and the jacket. The terminators are secured using epoxy and the braid is bound using a winding or wrap of thread. The braid does not contact the terminator or the coil, and floats electrically. A layer of a flexible tough material such as polyurethane is applied over the braid and onto the terminators.

7 Claims, 2 Drawing Sheets

INSERTION TUBE TERMINATOR

BACKGROUND OF THE INVENTION

This invention relates to borescopes or endoscopes, and is particularly concerned with construction of the tube body of the borescope or endoscope insertion tube. The invention is more particularly concerned with construction of the tube body with terminators at its proximal and distal ends which provides a continuous electrical ground path between the end terminators, but minimizes problems of leakage current through the walls of the tube body.

A borescope is generally characterized as an elongated flexible insertion tube with a viewing head at its distal or forward end, and a control section at its proximal end for controlling the bending at the distal end. In such a borescope, a bendable tube steering section is situated at the distal end adjacent to the viewing head. Typically, control cables extend through the bendable tube section and the remainder of the insertion tube and connect with a steering control mechanism in the control section. These cables are differentially displaced for bending the steering section to facilitate the inspection of a remote object.

A borescope is typically intended for visual inspection of an intricate mechanical assembly, such as a jet engine or turbine, or a heat exchanger tube, where it would be difficult or impossible otherwise to view the assembly's internal elements. The borescope needs to be insertable into narrow, tortuous passageways, and must observe very delicate steering considerations.

An endoscope is typically inserted into a body cavity of a human or veterinary patient for visual inspection of tissue within the cavity. Because body passages such as esophagus, bronchi, and colon are narrow and tortuous, the steering section must be bent rather precisely, and as close to the viewing head as possible.

Insertion tubes are designed to be torsionally stiff, and dimensionally stable both radially and axially. On the other hand, the insertion tube must be free to bend so as to follow contours of the machine passages or body cavities where it is employed.

In a number of applications of either a borescope or endoscope, ac leakage current through the insertion tube wall can affect a process or can endanger the health of a patient. This leakage current comes through capacitive effects with respect to the surroundings. On the other hand, a good ground path needs to be provided through the insertion tube body for providing an electrical ground to the miniature video camera and/or other elements situated at the distal tip of the insertion tube.

A typical insertion tube is constructed on an inner steel coil which provides radial stability (i.e., crush resistance) but still permits lateral flexibility for bending. A tubular layer of an elastomeric material, e.g. urethane, is disposed over this to seal the wall. Then tubular braid layer is positioned over the urethane tube to provide axial stability (i.e., stretch resistance) and torsional stability (twist resistance) and the tube is coated with a flexible insulating material, e.g. polyurethane.

In the past no effort was made to isolate the coil and braid electrically at the ends where a terminator element is attached to couple to a steering control or to the distal steering element. As a result, the only dielectric or insulating layer between the interior of the insertion tube and its environment was the thin layer or coating over the braid. This permitted levels of leakage current that were unacceptable for many procedures.

OBJECTS AND SUMMARY OF THE INVENTION

It is an object of this invention to provide a borescope or endoscope insertion tube, with end terminals, which is flexible but has good radial, axial, and torsional stability; which provides a continuous electrical path from one end terminal to the other end terminal; but which keeps to a minimum leakage current to the surroundings; and thus avoids drawbacks of the prior art.

According to an aspect of the invention, the insertion tube body has an inner helical metal coil, an insulating tubular elastomeric jacket over the coil, and a metal tubular braid layer disposed over the jacket. A terminator element having a metal sleeve portion is attached at each end of the tube body, with the sleeve portion being inserted at the respective end between the coil and the jacket. The coil and terminator sleeve portion are dimensioned for a good interference fit so that there is electrical contact between the terminators and the coil. The braid is trimmed so that the jacket extends to or slightly past the end of the braid and the braid thereby avoids electrical contact with the terminator or coil. The end of the braid is affixed, for example by winding with thread or monofilament, so there is a mechanical bonding of the braid end against the jacket, onto the sleeve portion of the terminator. Epoxy can also be applied onto the braid ends. Then, a layer of polyurethane or similar material is applied over the braid to penetrate the braid. This bonds with the urethane jacket and coats the braid to provide a smooth, tough outer skin.

The braid layer is electrically isolated from the coil and terminators. The effective dielectric layer between the coil and the outer environment comprises both the jacket and the outer polyurethane layer, with the braid layer "floating" electrically between them. Capacitive and resistive leakage currents can be reduced by fifty percent or more.

The total radial thickness of the tube body is no greater than previously, with only a small radial thickness increase at the locations of the terminators. A continuous ground path is provided through a coil between the proximal and distal terminators.

The thread wrap over the terminators creates a structurally solid mechanical pathway for the torsional load to pass from the terminator, through the plastic jacket, into the braid, which carries the torsional load in the tube body.

No special tools are required for fabrication, which keeps construction difficulty and cost as low as possible.

The above and many other objects, features, and advantages of this invention, will become apparent from the ensuing description of a preferred embodiment which is described in connection with the accompanying Drawing.

DETAILED DESCRIPTION OF A PREFERRED EMBODIMENT

Figure 1:
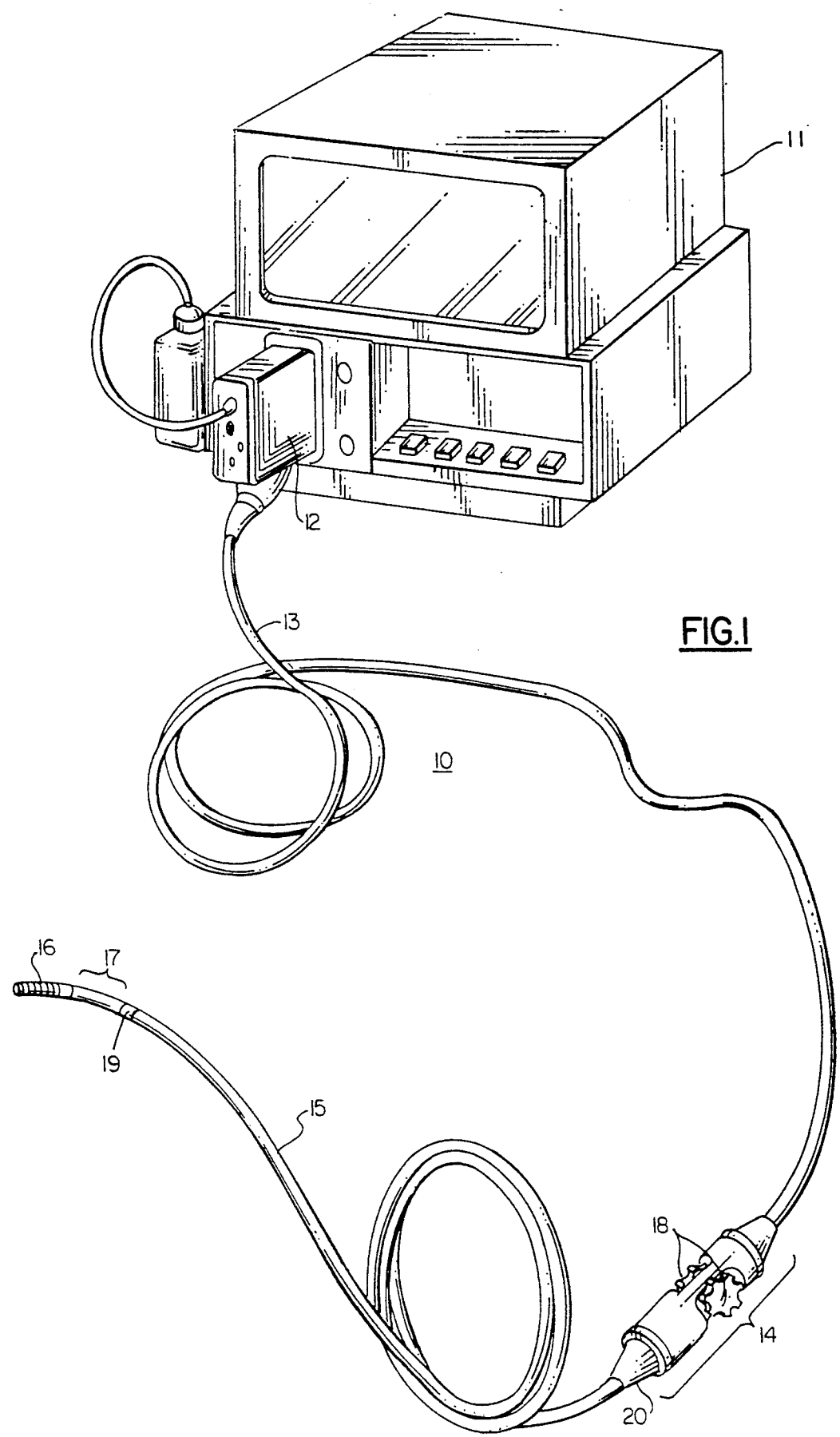
FIG. 1 is a perspective view of an endoscope having an insertion tube body according to one embodiment of this invention.

With reference initially to FIG. 1 of the Drawing, a medical endoscope 10 employs a video processor unit 11 with a connector module 12 that removably inserts into the processor unit 11. The module 12 is coupled by a flexible umbilical tube 13 to a steering control unit 14, to which is attached an elongated flexible insertion tube 15. A viewing head 16 is attached by a bendable steering section 17 to the distal tip of the insertion tube 15. A pair of steering control knobs 18 on the unit 14 move steering cables within the insertion tube 15 to control bending of the steering section 17, both side to side and up and down. Electrical conductors extend within the umbilical 13 and insertion tube 15 to carry power and synchronizing signals from circuitry within the module 12 distally to a miniature video camera within the viewing head 16, and also to bring video image signals from the miniature camera proximally to the connector module, from which they are fed to the processor 11 which produces a display of an object in the viewing field of the viewing head 16. An optical fiber bundle extends within the umbilical 13 and insertion tube 15 to bring illumination from the processor 11 to the distal end of the viewing head 16.

At a junction 19 of the insertion tube 15 to the bending section 17 there is a generally cylindrical metal terminator that joins these two elements together. Also, beneath a strain relief 20 at the distal side of the control unit 14 there is a similar terminator to join the insertion tube proximal end mechanically to the control unit housing.

Figure 2:
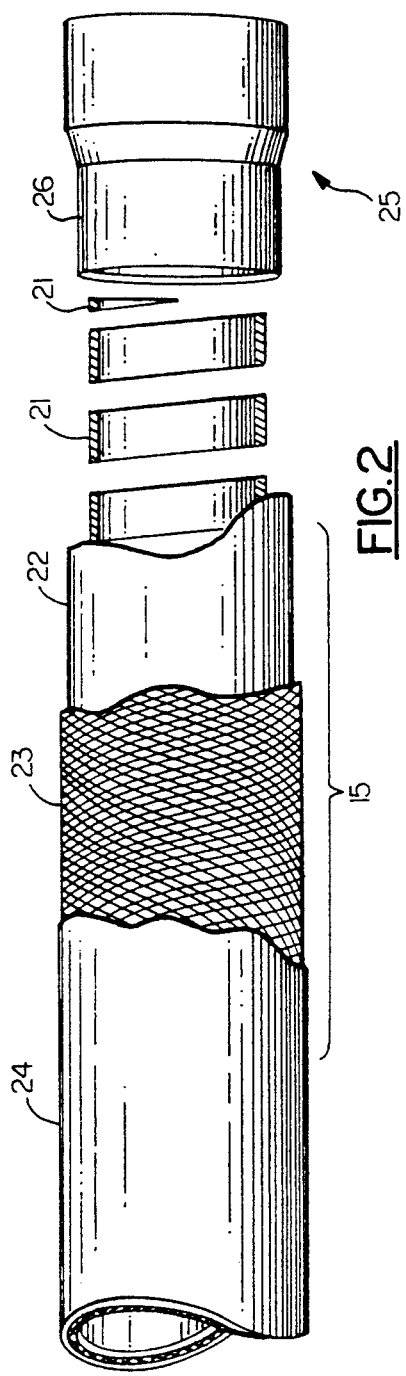
FIG. 2 is a partially cut-away view of one end of the insertion tube body showing construction thereof, the other end being of similar construction.
Figure 3:
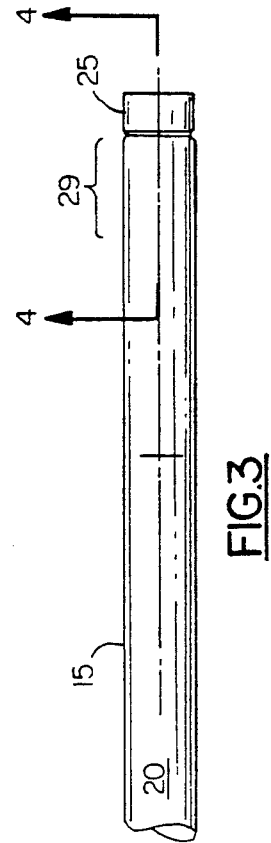
FIG. 3 shows one end of the insertion tube body, with end terminators.
Figure 4:
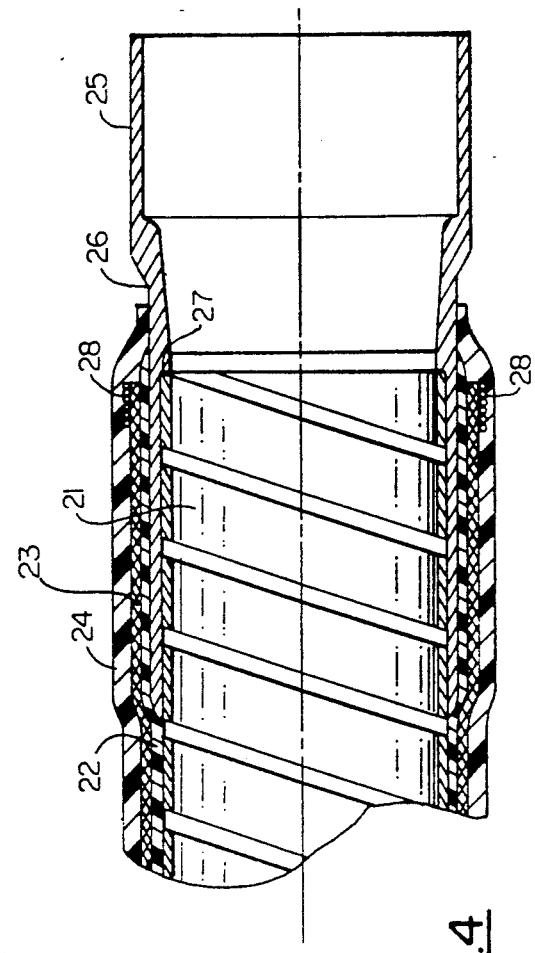
FIG. 4 is a cross section taken at 4—4 of FIG. 3.

The construction of the insertion tube body can be simply described with reference to the schematic view in FIG. 2, and as further illustrated in FIGS. 3 and 4.

The tube body 15 has a helical monocoil 21 extending throughout its length. The monocoil is formed as a helical ribbon of stainless steel, and provides radial dimensional stability. A tubular sleeve or jacket 22 of urethane or other plastic, elastomeric non conductive material is disposed over the monocoil 21 and a tubular braid layer 23 is disposed over the jacket 22. A coating 24 of polyurethane impregnates and adheres to the braid 23, and to the jacket 22, and is of sufficient thickness to form an outer skin for the insertion tube body 15.

An end terminator 25 is shown here at one end of the insertion tube body, but a similar or identical terminator would also be likewise attached on the other end. The terminator 25 is generally tubular so as to be symmetric about the axis. A smallest diameter sleeve portion 26 is inserted between the monocoil 21 and jacket 22 prior to coating with the coating layer 24. The sleeve portion has an inner diameter slightly less than the monocoil outer diameter so that there is a good interference fit between the monocoil 21 and the terminator 25 to achieve firm electrical and mechanical contact therebetween.

To attach the terminator 25, the end of the coil 21, jacket 22 and braid 23 is cut off square. Epoxy is applied to the inner diameter and the outer diameter of the sleeve 26 of the terminator 25. The terminator is inserted between the monocoil and jacket until the end of the monocoil 21 abuts an internal step or annular land 27 (See FIG. 4). Then, epoxy is applied onto the outside of the thin jacket 22 and the braid end is adjusted so that for a small distance the end of the jacket 22 projects axially beyond it. Then a wrap or winding 28 of monofilament is applied over the end of the braid and onto the jacket and terminator. Care is taken to avoid electrical contact between the braid 23 and the terminator 25.

After the epoxy has cured, the coating layer 24 of urethane is applied. The urethane penetrates the braid 23 and flows over the end of the braid onto the terminator 25, as shown in FIGS. 3 and 4.

The tubular steel terminators 25 incorporated at both the proximal and distal ends of the insertion tube body 15 connect respectively with the control unit 14 and the bending neck 17. The distal and proximal terminators 25 can be identical, which facilitates construction and inventory control.

At the position of the terminators 25 there is a slightly enlarged section 29 (See FIG. 3) but this is only about seven percent larger than the remainder of the insertion tube body, and there is no effective reduction in inside diameter. Electrical leakage characteristics, torsional strength, and flexibility are superior in the tube body 15 of the invention.

Leakage current is kept to a minimum because the braid 23 "floats" electrically, that is, the braid 23 is electrically isolated from the terminators 25 and from the monocoil 21. Both ac and dc leakage current must pass through the two insulating or dielectric layers formed by the jacket 22 and outer coating 24. The presence of the metal braid 23 does not impede significantly the leakage current to the environment.

There is a continuous electrical ground path between the terminators 25 and through the coil 21 to unite the bending neck 17 with the body or chassis of the control unit 14. The latter is grounded through a conductor within the umbilical 13 to the connector module 12 and thence to the chassis of the processor 11.

The tube body 15 enjoys good crush resistance and high torsional strength, especially at the junctions with the terminators 25. Torsional strength is provided by the relatively large shear area of the outer surface of the terminator sleeve 26, which is inserted into the tube body end. In addition, the winding or wrap of monofilament or thread 28 creates a sure mechanical path for torsional load to pass from the terminator 25 to the braid 23, whose function it is to carry torsional load in the tube body 15.

The distal terminal connects to the cable sheath terminator at the proximal end of the bending neck 17 and this connection is secured with epoxy. The proximal terminator connects to the tube connector of the control unit 14, and this connection can be carried out with set screws to allow circumferential adjustment or orienting the tube relative to the control unit. Then epoxy can be applied to make the connection permanent and fluid-tight.

While this invention has been described with reference to a preferred embodiment, it should be understood that the invention is not limited to that precise embodiment. Rather, many modifications and variations will present themselves to those skilled in the art without departing from the scope and spirit of this invention as defined in the appended claims:

What is claimed is:

1. A flexible elongated insertion tube body for a borescope or endoscope which has axial, radial, and torsional dimensional stability and provides electrical isolation between an interior and an exterior thereof, the insertion tube body comprising a tube body member which includes an inner helical metal coil, an insulating elastomeric tubular jacket disposed over said coil, a metal braid layer disposed over said tubular jacket, and an insulating coating applied onto said braid layer; a terminator in the form of a tubular member having a metal sleeve portion inserted at one end of said tube body member between said coil and said jacket and in electrical contact with the coil, said jacket extending axially to or beyond an axially terminal end of said braid so that the braid and coil are kept electrically isolated from one another by said jacket; and means mechanically binding said terminal portion of said braid onto said jacket over said sleeve portion of said terminator with said insulating coating extending over said terminal end of said braid.

2. The insertion tube body of claim 1 wherein said coil is a metal ribbon formed into an elongated helix having a predetermined inner diameter and outer diameter.

3. The insertion tube body of claim 2 wherein said terminator metal sleeve portion has an inner diameter smaller than said coil outer diameter so that said coil and terminator form an interference fit.

4. The insertion tube body of claim 2 wherein said terminator metal sleeve has an inner land against which an axial end of said coil is lodged.

5. The insertion tube body of claim 1 wherein said jacket is a tube of urethane.

6. The insertion tube body of claim 1 wherein said outer insulating coating is polyurethane which penetrates and covers over said braid.

7. The insertion tube body of claim 1 wherein said means mechanically binding includes a wrap of thread or monofilament wound over said braid terminal end.

* * * * *